United States Patent [19]

Conklin

[11] Patent Number: Plant 7,126

[45] Date of Patent: Jan. 30, 1990

[54] ROSE PLANT NAMED CONANGEL

[76] Inventor: Henry A. Conklin, P.O. Box 365, McFarland, Calif. 93250

[21] Appl. No.: 308,003

[22] Filed: Feb. 9, 1989

[51] Int. Cl.[4] ..... A01H 5/00

[52] U.S. Cl. ..... Plt./2

[58] Field of Search ..... Plt. 2

*Primary Examiner*—Robert E. Bagwill

[57] ABSTRACT

A new climbing sport of the floribunda variety "Angel Face", producing canes 6 to 9 feet in length.

1 Drawing Sheet

SUMMARY OF THE INVENTION

The present invention relates to a new and distinct variety of rose plant of the climbing floribunda class, which originated as a sport of the variety, "Angel Face" (U.S. Plant Pat. No. 2,792).

The new variety was discovered by me at my nursery in McFarland, Calif., in a cultivated area under controlled growing conditions. My attention was drawn to a plant that was presumed to be the variety, "Angel Face," but which exhibited definite climbing characteristics in that it produced canes which were 6 to 9 feet in length.

Asexual reproduction of this new variety by budding, under my supervision, at McFarland, Calif. has established that the climbing habit comes true to form and is transmissible and established through succeeding asexual propagations. The varietal denomination of the new variety is "Conangel".

The accompanying drawing shows a specimen plant of the new variety which is illustrative of the typical climbing habit of growth and the blooms produced.

In view of the fact that the new variety is distinguished from its parent only by its climbing habit of growth, it is unnecessary to describe the new variety in detail, since it conforms substantially to the detailed description appearing in U.S. Plant Pat. No. 2,792 dated Jan. 23, 1968, to which reference may be made and the content of which is specifically incorporated herein by reference.

I claim:

1. A new and distinct variety of rose plant of the climbing floribunda class, substantially as shown and described, which is a sport of the variety "Angel Face" (U.S. Plant Pat. No. 2,792) characterized particularly by its climbing habit of growth.

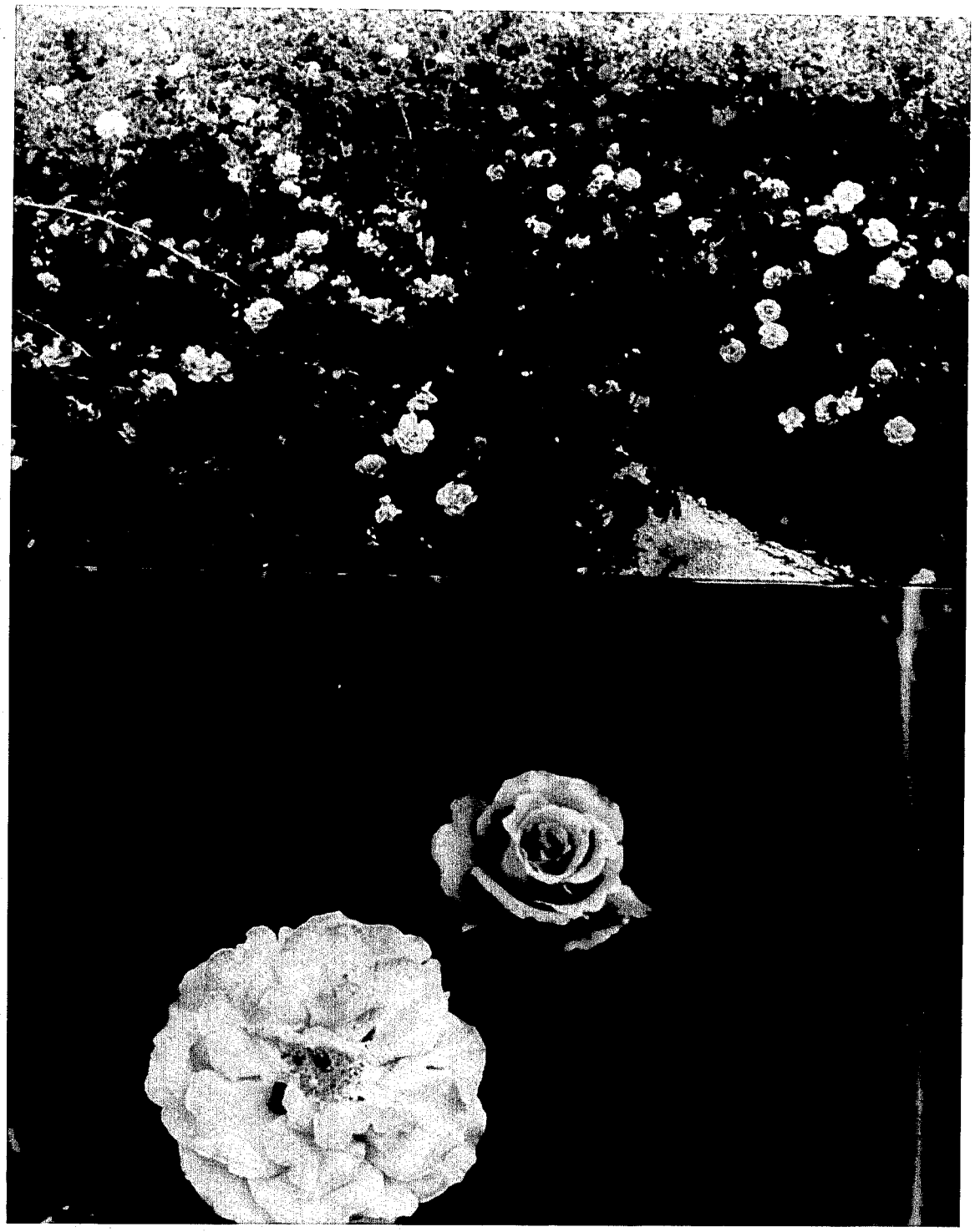

* * * * *